United States Patent [19]

Mohajer

[11] Patent Number: 4,906,261

[45] Date of Patent: Mar. 6, 1990

[54] SMOKE EVACUATION SYSTEM

[76] Inventor: Reza S. Mohajer, 1275 Orchard Ridge Rd., Bloomfield Hills, Mich. 48013

[21] Appl. No.: 321,376

[22] Filed: Mar. 10, 1989

[51] Int. Cl.$^4$ .................. B01D 29/08; B01D 53/18
[52] U.S. Cl. .............................. 55/256; 55/279; 55/356; 55/385.1; 55/466; 55/467; 55/482; 55/528
[58] Field of Search .................. 55/256, 274, 279, 356, 55/385.1, 385.2, 466, 467, 482, 505; 261/121.1

[56] References Cited

U.S. PATENT DOCUMENTS

| | | | |
|---|---|---|---|
| 1,719,255 | 7/1929 | Woodford | 55/467 |
| 2,115,482 | 4/1938 | Crewe | 55/467 X |
| 3,516,232 | 6/1970 | Gilbertson | 55/467 X |
| 3,695,012 | 10/1972 | Rolland | 55/467 X |
| 3,820,536 | 6/1974 | Anspach, Jr. et al. | 55/385.2 X |
| 3,847,573 | 11/1974 | Gandrud | 55/385.1 X |
| 3,860,404 | 1/1975 | Jochimski | 55/467 X |
| 3,890,126 | 6/1975 | Joseph | 55/385.1 |
| 3,923,482 | 12/1975 | Knab et al. | 55/467 X |
| 3,988,134 | 10/1976 | Gandrud | 55/385.1 X |
| 4,019,508 | 4/1977 | Der Estephanian et al. | 55/385.1 X |
| 4,023,472 | 5/1977 | Grunder et al. | 55/467 X |
| 4,092,136 | 5/1978 | Zimbardi | 55/467 X |
| 4,163,650 | 8/1979 | Watson et al. | 55/356 X |
| 4,251,485 | 2/1981 | Schauer et al. | 261/121.1 X |
| 4,350,507 | 9/1982 | Greenough et al. | 55/482 X |
| 4,487,606 | 12/1984 | Leviton et al. | 604/319 |
| 4,597,781 | 7/1986 | Spector | 55/505 X |
| 4,642,128 | 2/1987 | Solorzano | 55/467 X |
| 4,670,223 | 6/1987 | Delachapelle | 55/279 X |
| 4,690,699 | 9/1987 | Sugisawa et al. | 55/279 X |
| 4,701,193 | 10/1987 | Robertson et al. | 55/385.1 X |
| 4,735,603 | 4/1988 | Goodson et al. | 604/21 |

*Primary Examiner*—Robert Spitzer
*Attorney, Agent, or Firm*—Krass and Young

[57] ABSTRACT

A smoke evacuation system for use in surgical procedures in a surgical area is disclosed comprising a portable evacuation hood configured to be disposed proximate a surgical site for receiving gaseous by-products produced during the surgery. The evacuation hood contains a first filter disposed therein for trapping particulate matter. The smoke evacuation system further includes suction source in operative communication with the hood for evacuating the atmosphere from the hood. The suction source as well as a second filter associated therewith are externally disposed from the surgical area. Also disclosed is a portable evacuation hood for use in conjunction with the smoke evacuation system, which comprises a perforated inner wall and a solid outer wall having a chamber therebetween containing the first filter.

24 Claims, 3 Drawing Sheets

SMOKE EVACUATION SYSTEM

FIELD OF THE INVENTION

This invention relates to surgical equipment and more specifically to a system for removing smoke and other gaseous surgical by-products from an operation site. The system has particular utility in laser surgical procedures.

BACKGROUND OF THE INVENTION

Laser surgery has experienced an exponential growth in recent years. Approximately 4,000 laser surgeries per day are now being performed in the U.S. Lasers are being used in almost every conceivable kind of surgery, from correcting eye dysfunctions to removing warts and corns from the bottom of the foot. Laser surgery is also being increasingly utilized in cancer therapy as well, wherein cancerous tissue is vaporized by a laser beam of a preselected wavelength.

Laser surgery offers many benefits to the patient such as lower cost, reduced length of hospital stay and reduced recovery time since major incisions are often not as necessary as they are in conventional types of surgery. However, it now appears that laser surgery is posing serious health risks to the physician performing the surgery, the nurses attending the physician and the rest of the supporting personnel in the operating room. An increased number of lesions have been noticed in the personnel that perform or assist during laser surgeries. Lesions and other precancerous conditions such as papillomas and chondylomas are appearing at increasing rates on the face, eyes, nose, hands, lips and the larynx and lungs of those performing these surgeries.

During laser surgery of cancerous tissue the malignant tissue is vaporized by a laser beam. This vaporization produces gaseous by-products which can carry infectious, live virus into the surrounding air of the operating room. Gaseous by-products such as smoke can also be produced in conventional types of surgery wherein a surgeon uses an electric scalpel or thermal cauterizer during a surgical procedure. The smoke produced using these instruments often carries infectious virus into the atmosphere of the operating room as well as interfering with a surgeon's view of the surgical site. The live viruses or other materials contained in the gaseous surgical by-products can also adhere onto the eyes, skin and lungs of the personnel in the operating room, causing the above-mentioned lesions.

In laser surgery, a surgeon employs a high intensity laser beam of a preselected wavelength to vaporize infected or tumorous tissue. A smoke plume is often produced as a result of this vaporization. In heretofore employed techniques, the plume of gaseous by-products produced during this surgery was vented directly into the air of the operating room, possibly infecting those in the room. In some instances, a suction wand was maintained proximate the surgical site by an assistant; however these wands are generally rather narrow and hence not very effective at capturing the smoke plume. Additionally, such efforts have been found to interfere with the surgeon's actions. It is therefore desirable to provide a smoke evacuation system for effectively evacuating these infections, gaseous by-products produced during surgery.

U.S. Pat. No. 4,735,603 to Goodson et al. discloses an intra-abdominal laser smoke evacuation system and method for removing the laser smoke from the site of a laser laparoscopy. Disclosed therein is a closed-loop system wherein $CO_2$ gas is pumped through a Laparoscopic tube into a body cavity. The laser generated smoke mixes with the pumped-in $CO_2$ gas which is then vented through a second laparoscopic tube inserted into the patient. This intra-abdominal system removes only laser smoke produced during laparoscopic surgical procedures and requires insertion of at least two tubes into a patient's body as well as maintenance of a flow of $CO_2$ gas through the patient's body. This system requires a $CO_2$ gas pump, a discharge line connected with the pump, pressure sensors and inflators and is restricted solely to laparoscopic surgeries.

U.S. Pat. No. 4,487,606 to Leviton et al. discloses a suction canister assembly for aspirating and collecting liquids and gasses, produced during the surgery. The canister is a containment unit for receiving blood and other surgical by-products, but no means are provided for removing and/or sterilizing smoke produced at a surgical site.

It will thus be appreciated that there is yet a need for a smoke evacuation system which traps and evacuates all gaseous surgical by-products produced at a surgical site. The present invention addresses this problem by providing a smoke evacuation system for use in surgery which includes a portable evacuation hood for effectively trapping and evacuating gaseous surgical by-products at a surgical site. These and other advantages of the present invention will be readily apparent from the drawings, discussion, description and claims which follow.

SUMMARY OF THE INVENTION

There is disclosed herein a smoke evacuation system for use in surgical procedures in a surgical area comprising a portable evacuation hood which is configured to be disposed proximate a surgical site. The evacuation hood operates to remove the smoke produced at the surgical site. The system also comprises a first filtering means disposed in the hood for trapping particulate matter as well as microorganisms produced during the surgery. The system further comprises suction means external of the surgical area but in operative communication with the evacuation hood for evacuating the atmosphere therefrom. The system may also include an incinerator communicating with the suction means for destroying any surgical by-products passing from the suction means into the incinerator. In an alternative embodiment, the portable evacuation hood includes a perforated inner wall and solid outer wall. The hood defines a chamber between the inner and outer wall for receiving the first filtering means therein. The inner wall defines at least one opening in communication with the chamber and which is configured to permit gaseous surgical by-products to pass therethrough.

DETAILED DESCRIPTION OF THE PREFERRED EMBODIMENT

Figure 1:
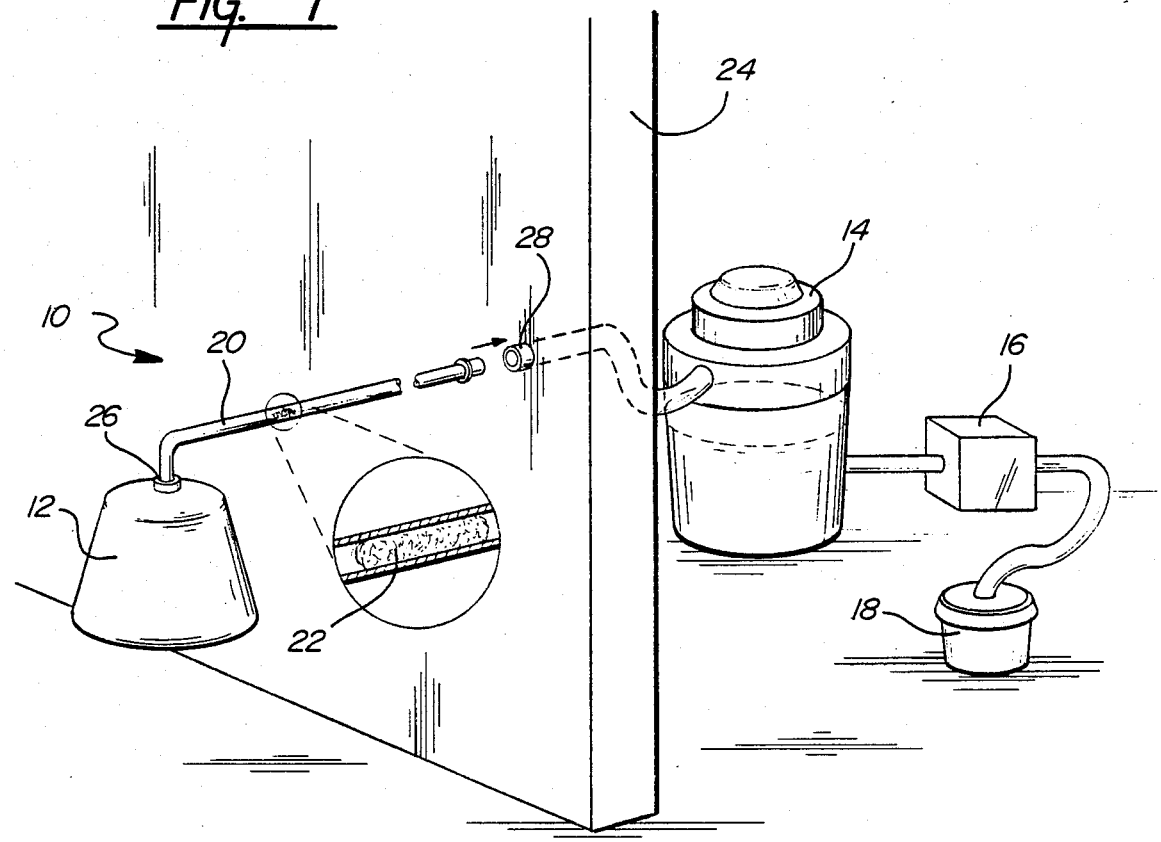
FIG. 1 is a perspective view of one particular embodiment of a smoke evacuation system structured in accord with the principles of the present invention.

Referring to the drawings: FIG. 1 is a perspective view of a smoke evacuation system 10 for use in surgical procedures in a surgical area such as an operating room or the like. The smoke evacuation system 10 comprises a portable evacuation hood 12 configured so as to be disposed proximate a surgical site. The system further includes first filtering means associated with the hood 12 (shown as 36,62 in FIGS. 2 and 3 respectively) as well as suction means such as a heavy-duty canister type vacuum cleaner 14 in operative communication with the evacuation hood 12. A second filter 16 is connected to the suction source 14 for trapping smoke and surgical by-products which may have bypassed the previous filters. An incinerator 18 or other such sterilizer may be associated with the second filter 16 for destroying and removing surgical by-products. A conduit 20, such as rubber or synthetic polymeric tubing, connects the evacuation hood 12 to the suction source 14.

Evacuation hood 12, which will be more fully described below, may be fabricated from a variety of materials including stainless steels, metals and most preferably from synthetic polymeric materials such as polyethylene, polystyrene, ABS or nylon. Evacuation hood 12 may be cup-shaped, bell-shaped or of any other similar shape and is configured so as to be conveniently hand-held by operating room personnel over a surgical site where smoke is being produced. Alternatively, the hood may be readily positioned by means of a mounting bracket or the like. Smoke is drawn into the evacuation hood 12 by means of suction produced through conduit 20 by the suction source 14.

The suction source 14 may be any of a conventional type of suction producing or aspirating device such as a conventional industrial vacuum cleaner often employed for surgical procedures. In the preferred embodiment, suction source 14, as well as the second filter 16 and incinerator 18, are disposed externally from the operating room behind wall 24. In utilizing this embodiment, possible contamination of the operating room is greatly reduced. However, the suction source 14 need not be disposed behind wall 24 and may be located in the operating room.

The plume of smoke generated in surgery is drawn into the hood 12, which, as will be described in greater detail hereinbelow, contains a first filter. The plume then passes through the conduit 20 to the suction source 14 which may include a filter, preferably a disposable, activated carbon filter. The exhaust from the suction source 14 enters the second filter 16. The second filter 16 is operative to destroy or inactivate any live virus or other microbial germs which pass into it. The second filter 16 contains an anti-microbial agent designed so as to kill bacteria and viruses. The anti-microbial agent may be impregnated onto a filter matrix or it may comprise a liquid through which the exhaust is bubbled. Types of anti-microbial agents and filters are well known in the industry and other conventional types of germicidal filters may be used. After passing through in the second filter 16, the exhaust stream may then pass into incinerator 18.

Incinerator 18 is configured so as to destroy all remaining surgical by-products which pass there into. Many conventional types of incinerators are commonly known in the industry and are used in surgical procedures. Incinerators such as an electric arc incinerator wherein an electric arc destroys the by-products may be employed as may be incinerators utilizing a stream of heated air, or a heated metallic or ceramic element maintained at a temperature sufficient to destroy any incoming by-products. Incinerator 18 is preferably configured so that it may be easily cleaned out and disinfected after each use.

Conduit 20 connects the evacuation hood 12 to the suction source 14. The conduit, typically of flexible tubing, is fitted by means of a swivel or ball joint 26 to evacuation hood 12. Swivel joint 26 allows operating room personnel to position evacuation hood 12 at a variety of different angles depending upon the direction the smoke travels during the surgical procedure. In the preferred embodiment, conduit 20 contains filtering material 22 for additionally filtering the gaseous by-products produced during the surgeries. The conduit 20 connects to a fitting 28 mounted in the wall for easy attachment and removal therefrom. Filtering material 22 contained in conduit 20 may be any conventional types of filtering means, such as a standard, non-woven, porous synthetic polymeric sheet with a maximum pore rating of 0.5 microns. This maximum pore rating allows for the filtering of particulate matter produced during the surgery including microorganisms.

Figure 2:
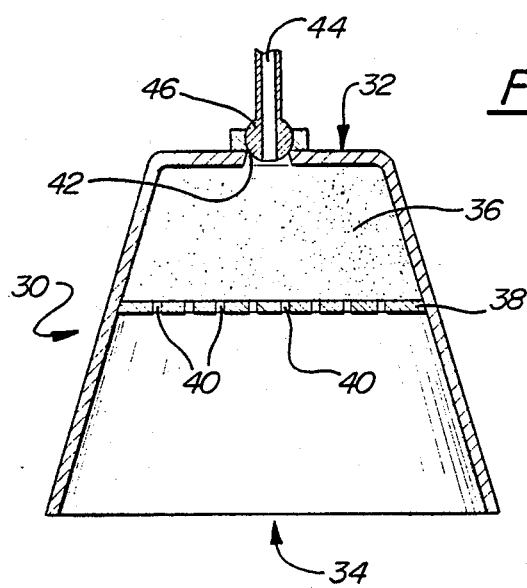
FIG. 2 is a cross-sectional view of a portable evacuation hood of the smoke evacuation system of FIG. 1 structured in accord with the principles of the present invention.

Referring now to FIG. 2, there is shown a cross-sectional view of an evacuation hood 30 of a smoke evacuation system as described in FIG. 1. Hood 30 defines a substantially closed top end 32 and an open bottom end 34 for receiving smoke therein. Hood 30 contains first body of filtering material 36 for trapping particulate matter such as microorganisms and other gaseous by-products produced during surgery. In the preferred embodiment, the filter 36 also may include a non-woven, porous synthetic polymeric sheet with a maximum pore rating of 0.5 microns. As above this pore rating is sufficient to entrap microorganisms which may be found in gaseous surgical by-products. Many other types of conventional filtering medium may also be employed in hood 30 such as those described in U.S. Pat. No. 4,487,606, the disclosure of which is herein incorporated by reference. Additionally, the filter 36 may include an antimicrobial material. Partition 38 is snap fit or otherwise secured into evacuation hood 30 for holding the first filter 36 in place and includes a plurality of openings 40 communicating with the filter 36. The openings 40 are configured to permit gaseous surgical by-products to pass therethrough.

The top end 32 of evacuation hood 30 defines an opening 42 for receiving conduit 44 therein. Opening 42 is configured so that a swivel or ball joint 46 may be placed therein and conduit 44 may be attached to it. Opening 42 is configured so as to define an air tight, non-leaking fit around joint 46 and conduit 44 to prevent the escaping of gaseous by-products from the system.

Figure 3:
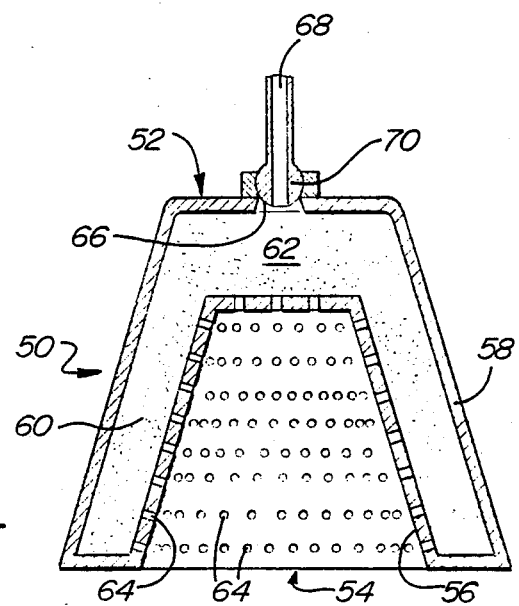
FIG. 3 is a cross-sectional view of another embodiment of a portable evacuation hood structured in accord with the principles of the present invention.

Referring now to FIG. 3, there is shown a cross-sectional view of an alternative embodiment of an evacuation hood 50 of the smoke evacuation system of FIG. 1. Evacuation hood 50 defines a substantially closed top end 52 and an open bottom end 54 for receiving gaseous by-products therein. Evacuation hood 50 also includes a perforated inner wall 56 and a solid wall 58 which cooperate to define a chamber 60 therebetween for receiving a first filter 62 therein. The inner wall 56 defines at least one opening 64 in communication with chamber 60, the opening being configured to permit gaseous surgical by-products to pass therethrough into chamber 60. As similarly described above, hood 50 defines an opening 66 at top end 52 for receiving conduit 68 therein. The opening 66 may also include a swivel or ball joint 70 for angular positioning of evacuation hood 50 in relation to the direction of travel of the smoke produced during surgery. Opening 66 defines an air tight seal between conduit 68 and joint 70 to prevent the escape of the surgical by-products therethrough. The first filter 62 is the same as described above, that being of sufficient pore rating to entrap microorganisms found in the gaseous by-products. Bottom end 54 of evacuation hood 50 in FIG. 3 as well as bottom end 34 of evacuation hood 30 of FIG. 2 may be threaded or otherwise configured for receiving additional conduit, such as a matingly engageable hood, to be attached thereto as shown in FIG. 6.

Figure 6:
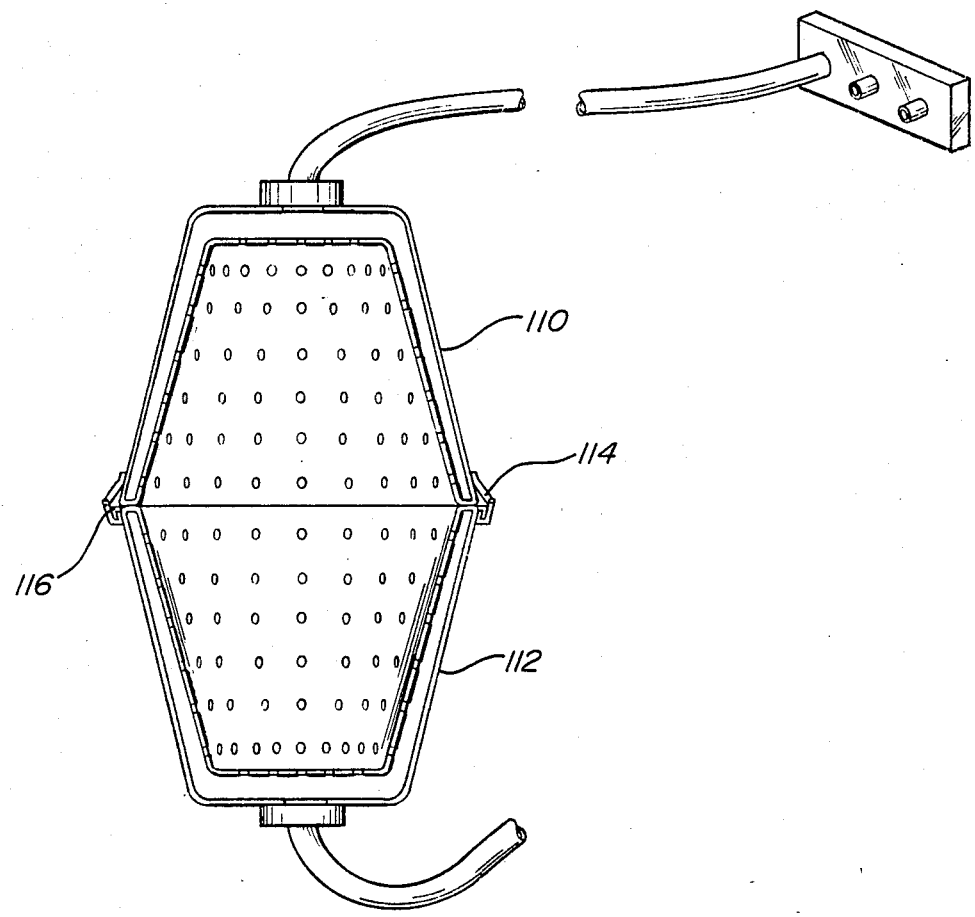
FIG. 6 is a perspective view of two portable evacuation hoods in matingly engageable communication.

In FIG. 6, two evacuation hoods, 110 and 112 respectively, are shown in matingly engageable communication to effectively form an airtight, in-line filtering mechanism for use with other surgical instruments utilizing suction filtration, such as my Vented Surgical Speculum disclosed in co-pending application, Ser. No. 251,790 and which is herein incorporated by reference. Hood 110 includes a latch 114 configured to be matingly engaged with projection 116 on hood 112 to effectively seal hoods 110 and 112 together. The seal between hoods 110 and 112 may include gasket material between the respective open ends to further ensure an airtight seal.

Alternatively, the open end of evacuation hood 110 may include female threads which are matingly engageable with male threads formed on the exterior surface of the open end of hood 112. Other types of engageable communication can be employed as well, such as a snap-fit relationship between the two ends of hoods 110 and 112. Other types of conduit, such as rubber tubing with an enlarged cross section, may also be fitted over the open end of hood 110 to form an in-line filtering mechanism.

Figure 4:
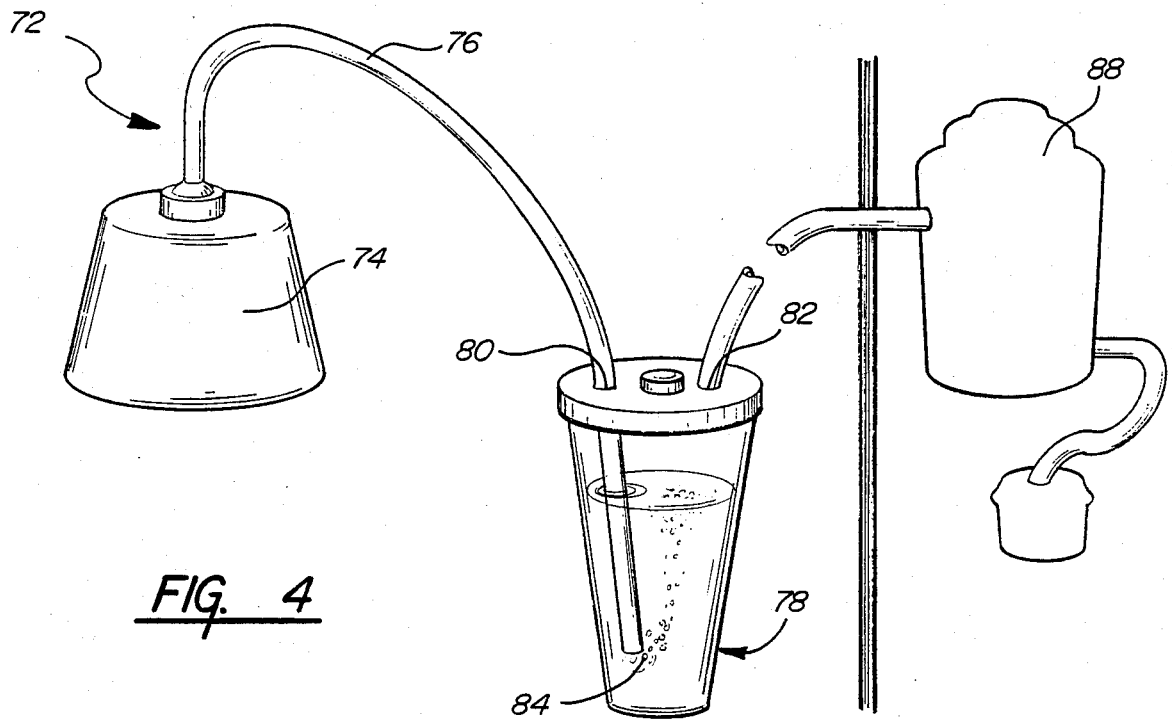
FIG. 4 is a perspective view of another embodiment of a smoke evacuation system structured in accord with the principles of the present invention.

Referring now to FIG. 4, there is shown an alternative embodiment of a smoke evacuation system utilizing a portable evacuation hood 74 in combination with a suction canister assembly 78. Conduit 76, typically rubber or vinyl tubing, connects evacuation hood 74 to an inlet port 80 of suction canister 78. Suction canister 78 may be any of a conventional type of suction canisters such as those described in U.S. Pat. No. 4,487,606. In the preferred embodiment, canister 78 is filled with either a liquid anti-microbial agent 84 or filtering means as described above, both capable of destroying bacterial and viral species. Canister 78 also includes an exit port 82 connected to suction source 88 as described in the earlier embodiment shown in FIG. 1. In use, suction source 88 produces a vacuum in suction canister 78 drawing smoke and other gaseous by-products through evacuation hood 74 and conduit 76 into canister 78 through inlet port 80. The smoke and other gaseous by-products are bubbled through the anti-microbial fluid which effectively destroys all live bacterial and viral microorganisms. Any remaining gaseous by-products are then drawn through exit port 82 and into a suction source 88 a described above. Suction canister 78 may also be employed during a surgical procedure to withdraw other liquid and solid surgical by-products produced during the surgery by means of an alternative suction tip.

Figure 5:
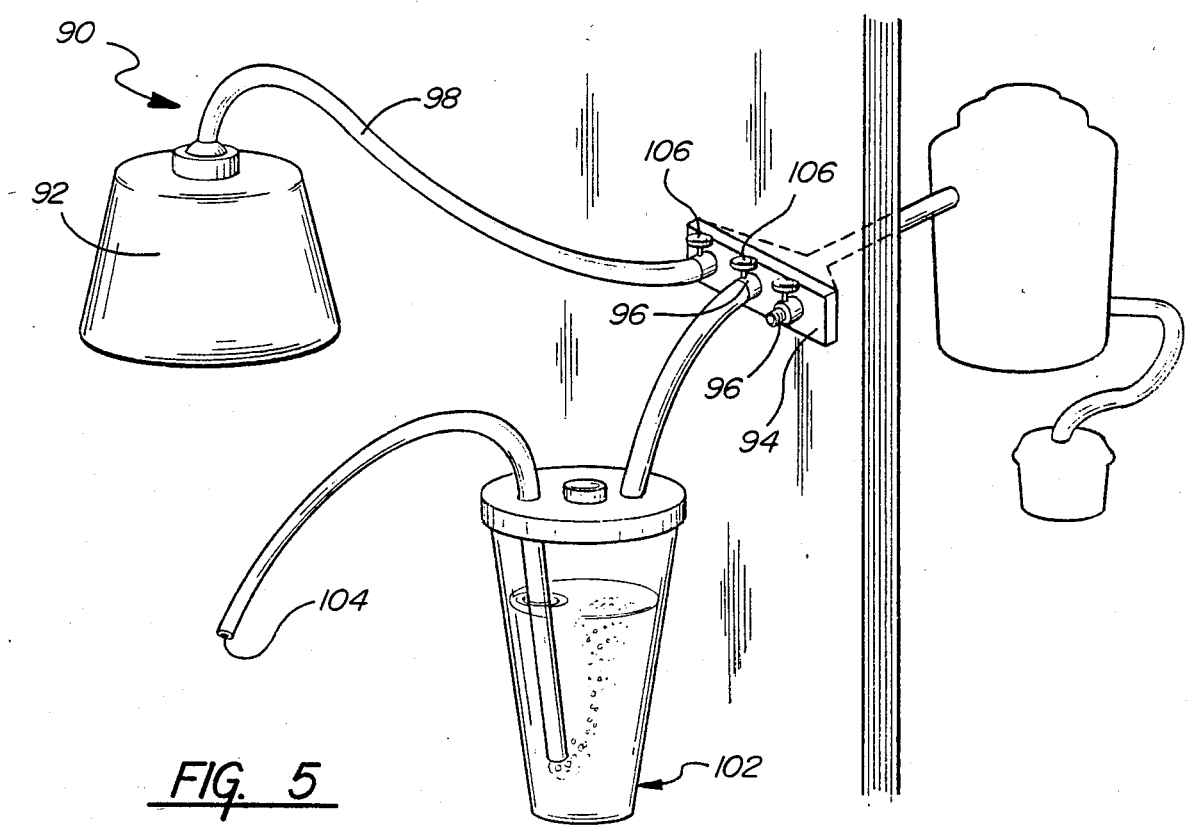
FIG. 5 is a perspective view of an alternative embodiment of a smoke evacuation system structured in accord with the principles of the present invention.

FIG. 5 shows a third embodiment of a smoke evacuation system 90 employing a manifold 94 which has a plurality of suction ports 96 for connecting various suction devices to suction means for use during surgical procedures. For example, a smoke evacuation system employing a portable evacuation hood 92 is connected to manifold 94 by conduit 98. For withdrawing liquid and solid surgical by-products, suction tip 104 is connected to manifold 94 through a suction canister assembly 102 as described above. In this embodiment, a surgeon is able to simultaneously withdraw all liquid, solid and gaseous surgical by-products without the need for changing the suction tips. Also, a surgeon can regulate the amount of suction through a portable evacuation hood or a liquid/solid suction tip by means of a regulator 106 located in manifold 94.

In light of the foregoing, it should be apparent that many variations are possible within the scope of the present invention. For example, smoke evacuation systems may be integral with liquid and solid evacuation system so as to allow all surgical by-products to be withdrawn through one suction device. Accordingly, the foregoing drawings, discussion and description are merely meant to be illustrative of particular embodiments of the invention and not limitations upon the practice thereof. It is the following claims, including all equivalents which define the scope of my invention.

I claim:

1. A smoke evacuation system for use in surgical procedures in a surgical area comprising:
   (A) a portable evacuation hood configured to be disposed proximate a surgical site for receiving smoke produced thereat;
   (B) first filtering means disposed is said hood for trapping particulate matter therein;
   (C) suction means in operative communication with said hood for evacuating the atmosphere therefrom, and said suction means externally disposed from said surgical area; and
   (D) second filtering means associated with said suction means for trapping smoke and surgical by-product therein.

2. A smoke evacuation system as in claim further including an incinerator in operative communication with said second filtering means for destroying surgical by-products passing therefrom.

3. A smoke evacuation system as in claim 2, wherein said incinerator includes an electric arc for destroying surgical by-products therein.

4. A smoke evacuation system as in claim 2, wherein said incinerator produces a stream of heated air of sufficient temperature to destroy said surgical products passing thereinto.

5. A smoke evacuation system as in claim 2, wherein said incinerator includes a heated body for destroying surgical by-products passing therethrough.

6. A smoke evacuation system as in claim 1, further including a conduit connecting said suction means to said evacuation hood.

7. A smoke evacuation system as in claim 6, further including a ball joint interposed between said conduit and said hood and operative to provide for angular displacement of said hood relative to said conduit.

8. A smoke evacuation system as in claim 6, wherein said conduit further includes filtering material contained therein for trapping particulate matter passing therethrough.

9. A smoke evacuation system as in claim 1, wherein said evacuation hood is fabricated from a material selected from the group consisting essentially of: synthetic polymeric materials, metals, stainless steels an combinations thereof.

10. A smoke evacuation system as in claim 1, wherein said first filtering means includes a non-woven, porous synthetic polymeric body with a maximum pore rating of 0.5 microns for filtering particulate matter including microorganisms passing therethrough.

11. The smoke evacuation system as in claim 1, wherein said second filtering means includes an antimicrobial agent.

12. A smoke evacuation system as in claim 1, wherein said evacuation hood includes a perforated inner wall and a solid outer wall and defines a chamber therebetween for receiving said first filtering means therein, said inner wall defining at least one opening therein in communication with said chamber and configured to permit gaseous surgical by-products to pass therethrough.

13. A smoke evacuation system as in claim 1, wherein said evacuation hood defines an open end configured so as to be matingly engageable with a second conduit.

14. A smoke evacuation system as in claim 13, wherein said second conduit includes a second evacuation hood having a matingly engageable end in communication with said open end of said evacuation hood.

15. A smoke evacuation system as in claim 1, wherein said suction means further includes a manifold configured so as to allow a plurality of suction devices to be added thereto 16. A smoke evacuation system for use in surgical procedures in a surgical area comprising:
(A) a portable evacuation hood configured to be disposed proximate a surgical site for receiving smoke produced in the course of surgery, said evacuation hood including a perforated inner wall and a solid outer wall defining a chamber therebetween, said inner wall defining at least one opening therein in communication with said chamber and configured to permit gaseous surgical by-products to pass therethrough;
(B) first filtering means disposed between said inner wall and said outer wall of said evacuation hood for trapping particulate matter therein;
(C) suction means in operative communication with said evacuation hood for evacuating the atmosphere therefrom, said suction means externally disposed from said surgical area;
(D) second filtering means associated with said suction means for trapping smoke and surgical by-products therein; and
(E) incinerating means in operative communication with said second filtering means for destroying surgical by-products passing thereinto.

17. A smoke evacuation system as in claim 16, wherein said incinerating means includes an electric arc for destroying surgical by-products contained therein.

18. A smoke evacuation system as in claim 16, wherein said incinerating means produces a stream of heated air of sufficient temperature to destroy said surgical products passing thereinto.

19. A smoke evacuation system as in claim 16, wherein said incinerating means includes a heated body for destroying surgical by-products passing thereinto.

20. The smoke evacuation system as in claim 16, further including a conduit connecting said suction means to said evacuation hood.

21. The smoke evacuation system as in claim 20, further includes filtering material contained in said conduit for trapping particulate matter passing therethrough.

22. The smoke evacuation system as in claim 16, wherein said first filtering means includes a non-woven, porous synthetic polymeric body with a maximum pore rating of 0.5 microns for filtering particulate matter including microorganisms passing therethrough.

23. A smoke evacuation system as in claim 16, wherein said suction means further includes a manifold configured so as to allow a plurality of suction devices to be added thereto.

24. A smoke evacuation system as in claim 16, wherein said evacuation hood defines an open end matingly engageable with a second conduit.

* * * * *

UNITED STATES PATENT AND TRADEMARK OFFICE
CERTIFICATE OF CORRECTION

PATENT NO. : 4,906,261

DATED : March 6, 1990

INVENTOR(S) : Reza S. Mohajer

It is certified that error appears in the above-identified patent and that said Letters Patent is hereby corrected as shown below:

Column 6, line 40, delete "is" insert --in--.

Column 6, line 50, after "claim" insert --1--.

Signed and Sealed this

Seventh Day of May, 1991

Attest:

HARRY F. MANBECK, JR.

Attesting Officer

Commissioner of Patents and Trademarks